United States Patent [19]

Demmin et al.

[11] Patent Number: 5,554,273

[45] Date of Patent: Sep. 10, 1996

[54] NEURAL NETWORK COMPENSATION FOR SENSORS

[75] Inventors: Hollis C. Demmin, Tonawanda; Richard B. Mazzarella, Grand Island; James D. Borkman, Clarence, all of N.Y.

[73] Assignee: Praxair Technology, Inc., Danbury, Conn.

[21] Appl. No.: 506,752

[22] Filed: Jul. 26, 1995

[51] Int. Cl.$^6$ .................................................. G01N 27/26
[52] U.S. Cl. ........................ 205/785; 205/775; 205/782; 204/408; 204/406; 395/21; 395/24
[58] Field of Search .................................. 204/408, 406, 204/403, 416, 418, 431, 432; 205/775, 782, 785; 395/21, 24; 128/635

[56] References Cited

U.S. PATENT DOCUMENTS

| | | | |
|---|---|---|---|
| 5,085,760 | 2/1992 | Razaq et al. | 204/431 |
| 5,121,443 | 6/1992 | Tomlinson | 382/29 |
| 5,177,994 | 1/1993 | Moriizumi et al. | 73/23.34 |
| 5,203,984 | 4/1993 | Sajai et al. | 204/435 |
| 5,225,063 | 7/1993 | Gumbrecht et al. | 204/402 |
| 5,247,445 | 9/1993 | Miyano et al. | 123/674 |
| 5,253,329 | 10/1993 | Villarreal et al. | 395/24 |
| 5,262,037 | 11/1993 | Markle et al. | 204/415 |
| 5,285,887 | 2/1994 | Hall | 198/460 |
| 5,352,348 | 10/1994 | Young et al. | 204/153.12 |
| 5,384,028 | 1/1995 | Ito | 204/403 |
| 5,387,328 | 2/1995 | Sohn | 204/403 |
| 5,389,217 | 2/1995 | Singer | 204/153.17 |
| 5,391,272 | 2/1995 | O'Daly et al. | 204/153.12 |
| 5,393,392 | 2/1995 | Masi | 204/153.16 |
| 5,393,401 | 2/1995 | Knoll | 204/418 |
| 5,395,503 | 3/1995 | Parce et al. | 204/403 |
| 5,429,727 | 7/1995 | Vogt et al. | 205/782 |

OTHER PUBLICATIONS

"VLSI Architectures for Neural Networks", IEEE Micro, Dec. 31, 1989, pp. 8–27.

"Model 3060E Ultra Trace Oxygen Analyzer Instruction Manual", P/N M59174.02, Teledyne Brown Engineering (May 23, 1994).

*Primary Examiner*—Bruce F. Bell
*Attorney, Agent, or Firm*—Cornelius F. O'Brien

[57] ABSTRACT

A method for correcting an output from an electrochemical cell sensor, having an output responsive to a concentration of sensed species in a stream, a pressure and a temperature in an interactive non-linear relationship, comprising the steps of providing a pressure sensor for producing an output responsive to a pressure in proximity to the electrochemical sensor; providing a temperature sensor for producing an output responsive to a temperature of said electrochemical sensor; and processing the outputs of the electrochemical sensor, pressure sensor and temperature sensor in a neural network having an output function which compensates said electrochemical sensor for changes in pressure and temperature to indicate a concentration of the sensed species. An apparatus is also provided, for compensating an electrochemical sensing apparatus, comprising an electrochemical sensor, being responsive to a sensed species, and an environmental variable; an environmental variable sensor, being responsive to said environmental variable; and a compensation network for producing a compensated output based on an output of said electrochemical sensor based and an output of said environmental variable sensor, said network comprising a neural network.

20 Claims, 6 Drawing Sheets

5,554,273

NEURAL NETWORK COMPENSATION FOR SENSORS

A portion of the disclosure of this patent document and appendices contain material which is subject to copyright protection. The copyright owner has no objection to the facsimile reproduction by anyone of this patent document or the patent disclosure, as it appears in the U.S. Patent and Trademark Office patent file or records, but otherwise reserves all copyright rights whatsoever.

FIELD OF THE INVENTION

The present invention relates to the field of compensation systems for electrochemical sensing-cell based concentration analyzers, and more particularly to neural network based compensation systems for electrochemical sensing cell gas analyzers.

BACKGROUND OF THE INVENTION

The ideal gas monitor will measure impurities in a supply gas stream accurately, with high precision and high reliability. However, real gas analyzers have accuracy and precision which are limited by ambient temperature, barometric pressure, gas pressure and other conditions that necessitate frequent calibration. For example, the temperature of the environment, e.g., room, which houses the analyzer has a large effect on the reading of most standard analyzers. Variations of as little as 5° F., such as between day and night, necessitate that the analyzer be calibrated at both temperatures in order to assure consistent results. Further, calibration requires that the analyzer be taken off line, disabling process measurements during the period of calibration. Of course, the frequency of calibrations also depends on the drift of the instrument and the sensitivity of the instrument to environmental changes. Likewise, barometric pressure, back pressure, and other conditions must be compensated in order to obtain reliable, consistent and accurate readings.

Some temperature induced variations, such as amplifier gain, may be easily compensated or eliminated to an insignificant level, using standard methods. Other variations, such as analyzer cell output, which are interactively affected by temperature and other factors, are not easy to compensate or eliminate.

The back pressure of the gas being sensed causes variation in analyzer cell output, in a manner not necessarily directly related to the partial pressure of the sensed species in the gas stream. This is due, for example, to a nonlinear response of the cell to increasing overall pressures. The standard method for compensating for back pressure is to employ a high cost process grade pressure sensor to accurately read the back pressure, allowing a correction without first separately compensating the transducer. Less accurate pressure sensors generally have limited applicability because of the importance of pressure compensation.

Present systems seek to compensate for or minimize temperature induced variation of the electronics by, for example, employing resistors, capacitors, and amplifier circuits which have low temperature coefficients, are temperature compensated or used in matched circuits. Resistors and capacitors, as well as other devices may be selected so that the temperature induced variations tend to be nulled or near linear under the conditions of interest.

The sensor cell of the analyzer, which is an electrochemical device, tends to be sensitive to many different factors, in addition to the gas being measured. The underlying chemical reaction may be non-linearly affected by temperature, and therefore the output will also vary non-linearly. For example, the chemical reaction kinetics may speed or slow with temperature, while diffusion, bulk transfer, or other factors may also be altered in a complex manner to alter the reaction or output.

The sensor may employ a liquid or a solid electrolyte. In general, electrolyte electrochemical sensors operate at higher temperatures to increase the mobility of the chemical species and conductance, and are therefore may be more sensitive to changes in temperature.

The causes of error in electrochemical gas analyzers are not well characterized. Therefore, while it is known that environmental variations do result in output variations, and that controlling these environmental variations may reduce the output variations, systems are not available which directly and adequately compensate the output for environmental variations. Thus, since a definitive model is not available, output compensation is not generally employed in high quality instruments, and rather error minimization through the use of environmental control and high quality compensating sensors is the approach taught by the art. Frequent calibration of "zero" and "span" is conducted to ensure accurate results. The use of gas analyzers tends to be mission critical and therefore fault intolerant and require high sensitivity, precision and accuracy.

Often, in order to eliminate the affects of temperature variation on the gas analyzer, the cell is placed in a constant temperature oven, which thermostatically regulates the operating temperature. This oven adds cost and bulk to the analyzer device, and increases the power consumption. The oven also does nothing to compensate for atmospheric pressure or back pressure, which are generally noncompensable according to the standard scheme, and which would in any case require the addition of expensive additional transducers and additional device complexity. Of note is that it would be extremely difficult to regulate the ambient pressure of the device, and the in-line process control usage of the device makes it difficult to control the back pressure. Thus, while temperature may be regulated, other factors still vary.

In an effort to reduce the cost of thermostatic ovens, low cost temperature sensors and switches may be employed, often resulting in less than optimal temperature control, and the need to calibrate the analyzer frequently.

Often, in order to electronically compensate the analyzer, devices are placed at critical locations. For example, a thermistor or thermocouple mounted in close proximity to or inside the cell senses the temperature at or in the cell. A thermistor has a resistance which varies with temperature, and may be used as a sensor in an electronic circuit that compensates the cell output. A thermistor is used because its nonlinear response to temperature may be used in a simple circuit to temperature compensate the sensor, and the electrochemical sensor and thermistor may be provided together as a replaceable, mostly interchangeable, unit. Therefore, a thermistor may be individually selected for each sensor, sensor lot or sensor type, to retain plug compatibility.

Therefore, because the analyzer output has a non-linear interdependence on sensed species, ambient temperature, back pressure, and other factors, adjustment for each independent factor by an independent adjustment leads to imperfect compensation. Further, the compensating devices themselves may have their own external dependencies which must also be compensated. For example, pressure transducers may be affected by ambient temperature. Further, due to the variety of sensors, reproducability from device to device will require individual, expensive calibration. Since the compensating device interactions may be non-linear, the compensating adjustments become extremely difficult and costly. In other words, high quality, high cost, internally compensated and linearized sensors may be employed, or a complex external compensation system must be employed. The art presently teaches against a unified compensation system due to its perceived cost and complexity, with the requirement that replaceable sensor components be interchangeable. The error budget of the apparatus is therefore apportioned between the individually compensated elements of the system, and high accuracy and precision sensors are employed which individually meet the requirements.

Neural networks are known processing systems for determining the solution to problems which are very difficult to handle by means of conventional logic systems. However, neural networks may be very difficult to validate or analyze, and therefore their use in "mission critical" applications may require extensive testing. Therefore, while conventional methods require complex algorithms, which explicitly formulate the relationship between input variables, neural nets "learn" the relationship between the variables. Neural networks may also require specialized hardware for acceptable performance, while the complex formulae of standard methods may be implemented with standard computing architectures. See, "VLSI Architectures for Neural Networks", IEEE MICRO, Dec. 31, 1989, pp 8–27, incorporated herein by reference.

U.S. Pat. No. 5,121,443 relates to a neural net system for analyzing chromatographic peaks. This reference discloses a system for characterizing a peak superimposed on a baseline.

U.S. Pat. No. 5,203,984, incorporated herein by reference, relates to a water quality monitoring system having an electrochemical cell which includes a neural network to improve precision. The water quality monitoring system of U.S. Pat. No. 5,203,984, however, does not disclose the use of a neural network to compensate a sensor for environmental variations, but rather to help process data from multiple chemical species-specific sensors to determine concentrations of the multiple species.

An artificial neural network (hereinafter "neural network") is a network of many processing elements ("units"), which may be implemented as parallel hardware or sequential processing on common hardware. The units are generally connected by unidirectional communication channels ("connections"), which carry numeric (as opposed to symbolic) data. The units operate on their local data and on the inputs they receive via the connections. Neural networks normally have great potential for parallelism, since the computations of the components are independent of each other. A neural network may therefore be either an algorithm, or actual hardware, whose design was motivated by the design and functioning of human brains and components thereof. See. FAQ in comp.ai.neural-nets, monthly posting, 28 Jan. 1995, incorporated herein by reference.

In a common type of neural net, the neural net includes input units, internal units (hidden layer) and output units. The input units are a first layer of the neural net. The internal units may be configured in one or more layers and the output units are the final layer in the net. Each of the input units supplies a signal to each of the internal units in the layer of the net adjacent to the input units. If the neural net has more than one layer of internal units, each unit in the first layer of internal units, i.e., the internal units receiving signals from the input units, generates an output signal that is provided to each internal unit in the second layer of internal units. Other layers of internal units are connected to adjacent layers of internal units in a similar manner. Each internal unit in the layer of internal units adjacent to the layer of output units provides a signal to each output unit. Each output unit provides an output signal.

For each neural net, the connections and/or weighting of connections must be provided so that for a given input pattern the neural net generates an appropriate output pattern. See, D. E. Rumelhart et al., "Learning Internal Representations by Error Propagation", in D. E. Rumelhart & J. L. McClelland (Eds.), *Parallel Distributed Processing: Explorations in the Microstructure of Cognition* (Vol. 1), pp. 318–362, MIT Press, 1986, Cambridge, Mass. See also, U.S. Pat. No. 5,253,329, incorporated herein by reference.

Most neural networks have some sort of "training", whereby the weights of connections are adjusted, using a form of feedback, on the basis of presented patterns and desired results. In other words, neural networks "learn" from examples, just like children learn to recognize dogs from examples of dogs, and exhibit some structural capability for generalization. Neural networks normally have great potential for parallelism in implementation, since the computations of the components are generally substantially independent of each other.

In theory, neural networks can be designed to compute any computable function, i.e. they can do everything a normal digital computer can do. In particular, anything that can be represented as a mapping between vector spaces can be approximated to arbitrary precision by feedforward artificial neural networks, a common type.

In practice, neural networks are especially useful for mapping problems which are tolerant of some errors, have a substantial amount of example data available, but to which hard and fast rules can not easily be applied. Neural networks are, at least today, difficult to apply successfully to problems that concern manipulation of symbols and memory. Where accuracy and complete characterization are desired, neural networks may also be difficult to apply.

Backpropagation of error, or "backprop", is a commonly used training method for neural networks. Backpropagation of error allows the neural network weights to "automatically" adjust based on a feedback of an actual result as compared to a result predicted by the neural network from a set of inputs. Because a model is not employed in defining these weights, the network may sometimes display artifacts or aberrant responses for input conditions which differ from training data, or model too closely the training data without regard for the true importance of any differences between an actual input condition and a training condition. Those skilled in the art therefore employ known techniques to optimize the training procedure.

Backpropagation of errors is often used for the training of layered (i.e., nodes are grouped in layers) feedforward (i.e., the data connection joining nodes are unidirectional, and there are no cycles) nets, often called "multilayer perceptrons".

Backpropagation of errors generally requires a "teacher" that knows the correct output for any input set ("supervised learning") and uses gradient descent on the error (as provided by the teacher) to train the weights. The activation function is (usually) a sigmoidal (i.e., bounded above and below, but differentiable) function of a weighted sum of the nodal inputs. The use of a gradient descent algorithm to train its weights makes it slow to train; but being a feedforward algorithm, it is quite rapid during the recall phase. Other types of training are also known.

"Overfitting" (often also called "overtraining" or "overlearning") is the phenomenon wherein the accuracy of the input/output relationship developed by the network decreases after a certain optimal point during training. This phenomenon arises because such long training causes the network to "memorize" the training patterns, including all of their peculiarities, whereas one is usually interested in the generalization of the network; i.e., the error it exhibits on examples not seen during training. Learning the peculiarities of the training set may therefore reduce the generalization capability of the neural network. The network should only be allowed to learn the general structure of the examples.

There are various methods used to fight overfitting. The two most important classes of such methods are regularization methods (such as weight decay) and early stopping. Regularization methods try to limit the complexity of the network such that it is unable to learn peculiarities. Early stopping aims at stopping the training at the point of optimal generalization. This latter method is typically achieved through the use of a pattern "test set". The original group of input patterns randomly split into two groups: the training set and the test set. While the training patterns drive the network weight changes, the test patterns are used only to monitor network performance. For a given iteration, the entire set of training patterns are presented to the network and the weights are adjusted accordingly. Next, the error over the test pattern set is calculated. The error for the training set will usually decrease with increasing iterations. The error for the test set, on the other hand, will typically reach a minimum when the generalization capabilities of the network are strongest. Beyond this point, the test set error increases, signifying that the network is overfitting the training patterns at the expense of learning the general relationship.

SUMMARY AND OBJECTS OF THE INVENTION

The present invention provides a system which provides a sensitive, precise and accurate gas analyzer which employs relatively low cost compensation sensors, and operates in a moderately controlled environment, producing valid and useful results through output compensation through the use of neural network technology.

The electrochemical sensor cell analyzer may be of standard type, such as the Teledyne model 3060, or of a type more optimized to take advantage of the improvements possible with the present invention. See "Model 3060E Ultra Trace Oxygen Analyzer Instruction Manual" P/N M59174.02, Teledyne Brown Engineering (May 23, 1994), incorporated herein in its entirety. See also U.S. Pat. No. 5,085,760, incorporated herein in its entirety. Another suitable electrode is described in U.S. Pat. No. 5,393,392.

The sensor to be compensated may also be of other types, including other electrochemical oxygen sensors, electrochemical sensors for other species, electrochemical devices which do not directly measure chemical species, and disparate other types of sensors. In order for the present invention to be most advantageously applied, the sensor should be repeatable and stable, and the significant sources of error must be known and subject to measurement.

For example, the sensor may be a semiconductive element which senses chemical species, and may be linked to biological systems or enzymes. Such sensors may have substantial nonlinearities, and may have complex interdependencies on a number of environmental factors. For example, enzyme couples ion sensitive field effect transistors, IS-FETs, have a nonlinear response to electrochemical potential, as well as responsiveness to a number of chemical species. An enzymatic-based sensor is also affected by the assay solution, the sensed species, and various modifying influences such as inhibitors and cofactors. Such a sensor, though subject to many factors, may be very repeatable. Further, the significant environmental influences may be measured. The neural network according to the present invention may then be trained for compensating these external dependencies and nonlinearities, and thereafter employed to compensate the sensor output. See U.S. Pat. Nos. 5,285,887; 5,387,328 and 5,393,401. See also, U.S. Pat. No. 5,395,503.

The present neural network compensation system may also be used to improve the performance of miniature electrochemical cells, such as medical catheter blood gas analyzers. In such a case, the electrochemical cell is subject to raw errors due to temperature variations, pH, buildup of oxygen and contaminants in the electrolyte, and effects to blood components. A neural network may be trained to compensate for these types of errors and linearize the output. See U.S. Pat. Nos. 5,225,063; 5,262,037 and 5,389,217. Such electrochemical cells may also be used to measure other species, based on intrinsic cell specificity or coupling to a specific factor, such as an enzyme. See U.S. Pat. Nos. 5,352,348 and 5,391,272.

The compensation neural network is trained through supervised training in an environmental chamber with varying conditions of operation encompassing the range of environmental conditions likely to be experienced by the analyzer during use. In this way, the network may be trained to appropriately generalize the discrete training conditions to the full range of actual environmental variation. Because of this multivariate compensation, the compensation sensors need not be laboratory or process grade devices, and in fact the environmental sensors may be compensated along with the entire instrument, in the neural network compensator. Thus, while it is desirable that each of the sensing elements, especially the electrochemical gas sensor, be repeatable and precise under given circumstances, the present design allows relaxation of the required accuracy of the sensing systems.

If the sensors display hysteresis or other types of historical dependance on input, the neural network may also include compensation for these path dependencies, although it is preferred that the sensors have low hysteresis so that this added complexity is avoided.

Thus, uncompensated sensors or those with otherwise unacceptable external dependencies may be employed, so long as the outputs are repeatable for given input conditions and the significant external dependencies are determinable by one or more sensors providing input to the compensation network.

The present system provides for the use of a plurality of sensors, including the electrochemical gas analyzer cell, pressure sensor and temperature sensor, which may not be fully externally compensated and may have non-linear interaction. The sensor outputs are fed to a neural network, which is trained for the output characteristics of the various sensors, to produce an output which is compensated for the sensed conditions and linearized.

Because the network is trained for these interactions, in large part the individual sensors may be replaced with a simple secondary calibration procedure, rather than a full retraining. Further, because a neural network is employed, when the analyzer is recalibrated, the neural network may be updated to learn the new conditions. Therefore, device aging, and especially electrochemical cell sensor aging may also be compensated intelligently.

The complex integrated compensation system eliminated the requirement that the sensors employed be separately compensated and linearized. Thus, substantial cost and complexity savings may be obtained. The characteristics of the low cost sensors, as well as the analyzer itself, are learned by the neural network over varying operating conditions. All of the various interactions are learned simultaneously. The results may be more accurate than prior art systems.

The present system employs a sophisticated compensation network, so that the linearity and independence from external dependencies of the primary sensor of the analyzer is not critical. Rather, the repeatability, freedom from hysteresis, baseline stability and freedom from oscillation are important, because these factors are difficult or impossible to correct in the compensation network. Thus, low cost sensing elements which do not include internal compensation or individual calibration may be used. Further, even when employing such low cost sensing elements, the need for zero and span adjustments is minimized. External dependencies which would limit the accuracy of the most sensitive ranges of the analyzer are compensated by the network, therefore, lower levels of a component may be reliably measured in gas streams.

While individual cells of the same type may differ somewhat in their output and sensitivity, in general, their higher order dependence on external variables will remain qualitatively similar. Since the neural network is trained for these dependencies and interactions, in large part the individual sensors may be replaceable with a simple secondary calibration procedure, rather than a full neural network retraining. In other words, the neural network training weights may be integral to the analyzer, with a relatively simple procedure for updating the compensation system as the sensors are replaced or modified. For example, if a copper-constantan thermocouple is employed for temperature sensing, likely no special calibration will be necessary if this sensor is replaced, as this sensor is well characterized and repeatable between units of the same type. Semiconductor temperature sensors may be provided with, e.g., 1 to 4 calibration coefficients. A replacement pressure sensor may be provided with a small amount of calibration data, such as 2 to 64, or more coefficients. These coefficients may be provided as information with the sensor, which is input into the compensating apparatus when the sensor is replaced, in a machine readable form, such as a PROM, EPROM, EEPROM, FRAM, flash memory, floppy disk, bar code, 2D code, optical code, or other method. Advantageously, in semiconductor sensors, the calibration data may be included integral to the sensor as analog or digital information. This calibration information need not update the coefficients of the neural network, but rather conform the actual sensor to the prototype sensor for the neural network. This calibration may then be computed as a preprocessing step before application in the neural network. This calibration data may be collected from the sensor alone, over a limited range of environmental and sensed variable conditions, rather than in the context of the instrument as a whole, simplifying the calibration procedure. A sensor having a data storage memory is disclosed in U.S. Pat. No. 5,384,028.

The electrochemical cell itself generally has a greater dependence on external factors, and therefore requires a larger amount of calibration data. Therefore, in this instance, the cell may include either calibration coefficients, or new or supplementary data for the neural network. Therefore, a prototype neural network may be provided in a calibration apparatus, based on training data from a prototype electrochemical cell. The new cell may then be subjected to a relatively small number of selected environmental conditions, the results of which are used to compute an optimal neural network. The neural network coefficients are then provided with the sensor, such as stored in an EEPROM, and input into the compensating apparatus upon replacement of the sensor. Alternatively, the calibration data included with the sensor may be supplementary to the neural network programming, for defining the differences between the prototype electrochemical cell and the replacement electrochemical cell.

Of course, when the electrochemical cell is used in an analytical instrument, such as for the detection of oxygen levels in process gas for semiconductor fabrication, the gas analyzer with a full complement of compensating sensors may be used to train a neural network individually for that instrument. On the other hand, where production volume and cost are significant considerations, and therefore individual full compensation is untenable, such as for commercial carbon monoxide monitors, a prototype sensor compensation system may be established with a final calibration of the instrument as a whole with a small amount number of conditions, such as zero and span, at standard temperature and pressure (STP).

In an analytical instrument, where periodic calibration is conducted, the neural network may be periodically updated by a learning algorithm to adapt to the actual conditions and characteristics of the sensors, which may change over time. Therefore, device aging, and especially electrochemical cell sensor aging may also be compensated intelligently. For example, if the analyzer is calibrated once each day for zero and span, these corrections may be learned, in order to minimize errors. Further, once the external dependencies are compensated, it is possible to use predictive modeling to improve the effective response time of the instrument, and to provide an earlier indication of undesired or unexpected process changes. When these external dependencies are not compensated, such predictive modelling leads to a substantial increase in noise.

Because of the complex integrated compensation system, sensors employed need not be individually compensated and linearized. Thus, substantial cost and complexity savings may be obtained. In fact, certain types of sensor compensation are undesirable. For example, a piecewise approximation to linearize a sensor may result in artifacts in the neural network. The characteristics of the low cost sensors, as well as the analyzer itself, are learned by the neural network over varying operating conditions. All of the various interactions are learned simultaneously. The results may be more accurate than prior art systems.

As an alternative to the simple neural network according to the preferred embodiment, other types of neural networks may be employed, such as General Regression Neural Networks, or recurrent networks.

The neural network compensation technique may be used in other circumstances to improve sensor output accuracy. For example, a combined sensor may detect multiple gas streams, such as process and control/calibration. While a dual cathode oxygen sensor may internally compensate for first order and/or higher order sources of error, residual errors may still be present, and indeed some sources of raw error in a dual cathode design may exceed those in a single cathode design. A multiple input sensor design may be used to match the unknown with a known, to "null" the output, to provide a compensating input and a sample input, and to provide a "switching" sensor design where two symmetric inputs are periodically each used as control/calibration and unknown.

The neural network sensor compensation system according to the present invention may also be used with sensors other than oxygen sensors. For example, electrochemical reducing gas sensors, such as carbon monoxide and hydrogen sulfide, as well as ammonia, arsine, and other types of chemical compound sensors may be compensated using neural networks. Further, a class of sensors known as ion sensitive field effect transistors may also be compensated using neural networks. Other semiconductor-based and biological material-based sensors are subject to corresponding considerations, and compensated accordingly.

Finally, the neural network compensation system according to the present invention may be used to compensate and linearize thermistor, hot wire or thermocouple sensors, e.g., thermal conductivity sensors, paramagnetic oxygen ($O_2$) analyzers, flame ionization analyzers, non-dispersive infrared analyzers for carbon monoxide and carbon dioxide, and other sensors, for known or presumed sources of variability.

For a full understanding of the present invention, reference should now be made to the following detailed description of the preferred embodiments of the invention as illustrated in the accompanying drawings.

DETAILED DESCRIPTION OF THE PREFERRED EMBODIMENTS

Figure 1:
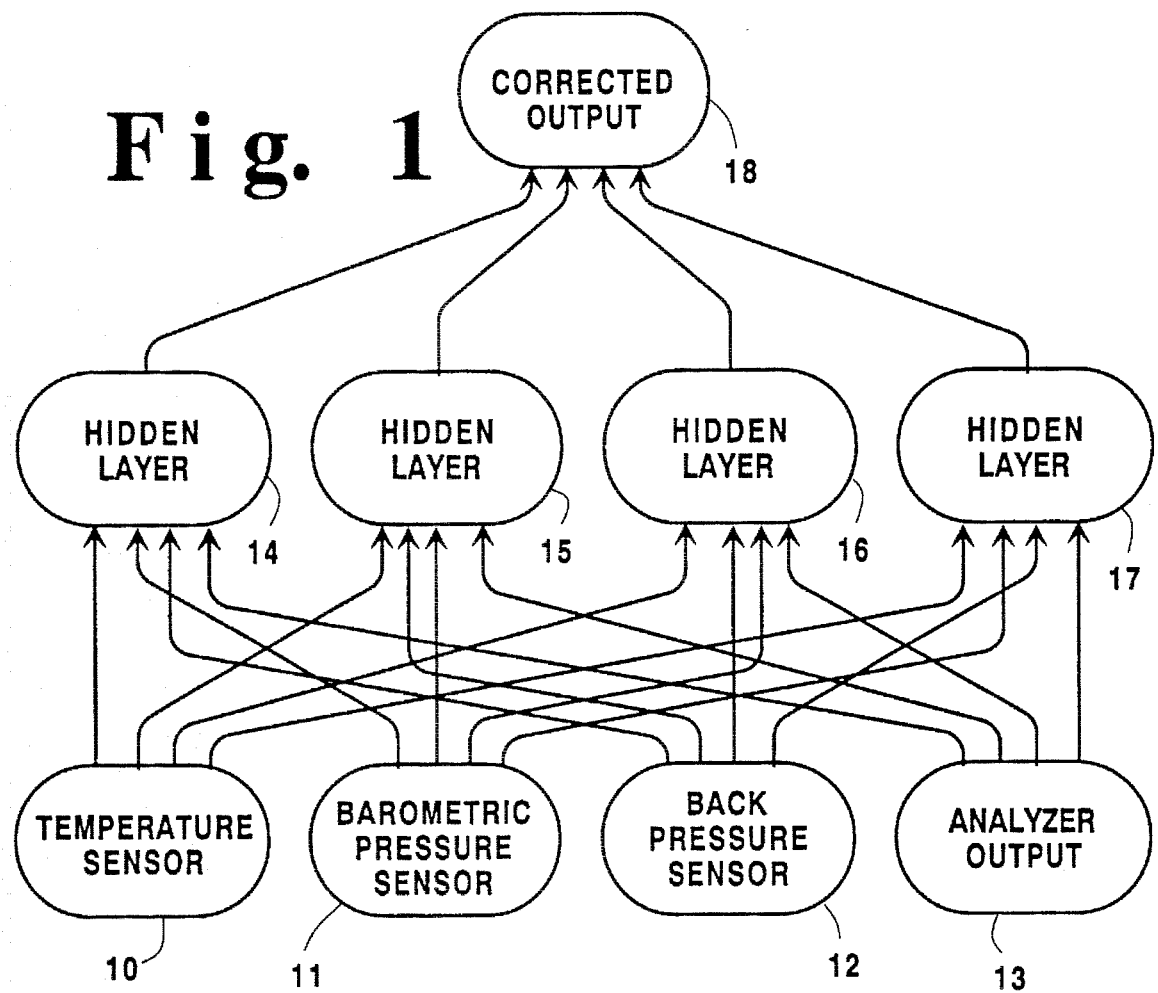
FIG. 1 diagrammatically shows the structure of the neural network of the present invention.

The preferred embodiments of the present invention will now be described with reference to FIGS. 1–7 of the drawings. Identical elements in the various figures are designated with the same reference numerals.

EXAMPLE 1

In a preferred embodiment, a gas analyzer instrument, having an electrochemical oxygen sensing cell, e.g., a Teledyne model 3060E is further provided with a copper-constantan thermocouple temperature sensor, and a process type differential pressure transmitter, e.g., a Rosemount model 1151GP4E2281, along with accompanying conditioning electronics, connected to a data acquisition system.

For initial training of the neural network, the analyzer and sensors are placed in an environmental chamber, with control over temperature and back pressure.

The analyzer is supplied with a gas stream having an oxygen concentration between 0 and about 10 ppm oxygen in nitrogen, e.g., 0, 2, 5 and 9.5 ppm. The gas stream is also provided with a back pressure of between 0–25 inches of water. The pressure in the chamber is varied over a normal atmospheric range, e.g., between about 700–820 mm Hg.. Ambient temperature is varied over the range 55 to 90 F.

The gas concentration may also be varied over the range 0–9.5 ppm by providing a source of pure nitrogen and a source of 9.5 ppm oxygen in nitrogen and employing a dynamic dilution system containing mass flowmeters to generate the intermediate concentrations.

Alternately, a Faradaic calibrator system and oxygen scrubber may be used to provide the calibration gas. The oxygen scrubber ensures a gas stream with a normally undetectable oxygen concentration, to which may be added a known concentration of oxygen by hydrolyzing water with a known current. A mass flow sensor determines the flow of gas to determine the resulting concentration. Such a system is included in the Teledyne 3060E.

The instrument is stabilized for an appropriate period, e.g., 1–3 days in the sensing chamber with 0 ppb oxygen. The data collection is then performed, either manually or automatically. The full range of each variable is explored, with varying conditions for all independent variables. The full range may also be explored through random selection of test vectors or a statistical or scientific determination of optimum test vectors. Duplicate measurements for each set of test conditions is not generally necessary, and a greater variety of different tests is preferred for the same number of tests.

The obtained data is then used to train the neural network through a backpropagation of error paradigm. The preferred neural network is a three layer feedforward neural network. The data was fed into a Ward Systems neural network tool, NeuroShell. The parameters produced are used with Ward Systems Runtime package to create Basic language code. The resulting code is loaded into an Octagon Systems model 7200 single board computer a STD bus single board computer. The Octagon 7200 includes a 64180 microprocessor, 12 bit analog to digital converter and 12 bit digital to analog converter. It also includes an RS-232 serial port. Therefore, conditioned sensor data is fed directly to the computer, where the data is processed to compensate the analyzer output, and the output is provided to the serial port as ASCII codes for formatted display, and may also output to a 4–20 mA loop, for use in standard process control systems. The Basic code is provided as an appendix hereto.

DESIGN AND TRAINING OF THE NEURAL NETWORK

The design of the neural network compensated analyzer is shown in the following Table. When designing a neural network analyzer, it is important to ensure that the training data is accurate and representative of conditions of actual use. Further, it is important to ensure that the significant sources of error are controlled, so that the compensate output is meaningful. The protocol shown in the Table is directed to achieving these goals.

TABLE

Design the Experiment 1.1 Select the analyzer
    1.1.1 Teledyne 3060
    1.1.2 Specifications
        1.1.2.1 1 PPB (50 PPB Range) Sensitivity
        1.1.2.2 +/−5% accuracy over 41 to 104 F. temperature range
        1.1.2.3 +/−2% accuracy at constant temperature
1.2 Select extraneous factors
    1.2.1 Oxygen concentration
    1.2.2 Ambient temperature
    1.2.3 Barometric pressure
    1.2.4 Back pressure
1.3 Select number of tests
    1.3.1 Experimental design techniques
1.4 Select test ranges
    1.4.1 0 to 375 parts per billion of oxygen
    1.4.2 55 to 90 degrees Fahrenheit
    1.4.3 0 to 25 inches of water for back pressure
    1.4.4 700 to 820 mm Hg for barometric pressure Conduct the tests 2.1 Environmental room
    2.1.1 insulated room
    2.1.2 Air conditioner to provide cooling
    2.1.3 Heater to provide heat
    2.1.4 Temperature control system
2.2 Data Acquisition System
    2.2.1 Fluke Helios
    2.2.2 Personal Computer
    2.2.3 Labtech Notebook software
2.3 Dilution system to vary the oxygen concentration
    2.3.1 Mass flow controllers Train neural network 3.1 Select meaningful data
    3.1.1 140 runs were made
    3.1.2 23 sets of data selected
3.2 Format the data for the neural network
    3.2.1 collect data in Lotus spreadsheet format
3.3 Commercial neural network used to analyze the data
    3.3.1 Ward Systems neural network tool, NeuroShell
    3.3.2 The number of iterations is determined according to standard practices in neural network training Produce neural network code 4.1 Present trained neural network to Ward Systems Runtime package to generate BASIC language computer code
    4.1.1 Code run on single board computer to correct the actual readings to true values
        4.1.1.1 For example, 0.2 PPM reading from oxygen analyzer might equate to 0.16 PPM actual oxygen at the current temperature and pressure conditions Implement single board computer code 5.1 Develop code to read transducers and analyzer outputs
    5.1.1 Using BASIC language computer code, assign channels for the single board computer to the various test parameters
        5.1.1.1 For example, channel 1 is the temperature sensor, channel 2 is the analyzer output, channel 3 is the back pressure transducer output and channel 4 is the barometric pressure
    5.1.2 Apply scaring factor to preprocess sensor output data
        5.1.2.1 For example, 2.00 V on channel 1 is 75 F., 1.00 V on channel 2 is 10 PPB, 2.45 V on channel 3 is 23 inches of water back pressure and 4.64 V on channel 4 is 30.10 inches of water barometric pressure
5.2 Integrate the neural network computer code into this pregrain so the values from the transducers can correct the analyzer output
5.3 Develop computer code to display the correct analyzer output
5.4 The result of the neural network correlation is displayed as a true value on a digital display Assemble hardware 6.1 Single board computer
    6.1.1 Octagon Systems Corporation Model 7200
6.2 Power supply
6.3 Hardware assembly
6.4 Input/output wiring Implement the system In step 1.1, an analyzer, the Teledyne 3060 trace oxygen analyzer, is selected which is standard for the intended use, and representative of a state of the art instrument which will demonstrate improvement from improved compensation for environmental conditions. Based on experience and known information, environmental conditions 1.2 which effect the output of the analyzer, including the measured variable, oxygen concentration 1.2.1, ambient temperature 1.2.2, barometric pressure 1.2.3 and back pressure 1.2.4.

The number 1.3 and characteristics 1.4 of data points of the test are selected in accordance with standard experimental design principles 1.3.1, to provide an optimal variety of test conditions 1.4.1, 1.4.2, 1.4.3 and 1.4.4. without conducting superfluous tests.

The environmental conditions to be tested are simulated in a controlled environment 2.1, including an insulated room 2.1.1, an air conditioner 2.1.2, a heater 2.1.3 and a temperature control system 2.1.4.

A data acquisition system 2.2 is provided including a Fluke Helios system 2.2.1, a personal computer 2.2.2 and Labtech Notebook data acquisition software 2.2.3. This system receives data from the oxygen analyzer, temperature sensor, back pressure sensor and barometric pressure sensor.

A dilution system 2.3 is provided for accurately generating oxygen concentrations in a flowing gas. Low oxygen amounts may be generated accurately in a Faradaic cell, by hydrolyzing water with a known current. This known quantity of oxygen is diluted in a flowing stream of inert gas, such as Nitrogen. The Nitrogen flow is measured with mass flow controllers 2.3.1, which may be a hot wire anemometer or other type.

The resulting data set includes the known oxygen concentration is the gas stream, the test conditions, the measured oxygen concentration, the measured temperature, the measured back pressure and the measured barometric pressure, are used to train the neural network 3, by analyzing them ensure that meaningful data is selected 3.1. In this case, 140 runs were made 3.1.1, and 23 sets of data selected 3.1.2. This data is then formatted in Lotus spreadsheet format (WKS format) 3.2.1, and applied to an available neural network tool, Ward Systems NeuroShell 3.3.1, with the number of iterations determined according to standard practices. Neural network code is generated 4, using the Ward Systems Runtime package, to produce executable BASIC code 4.1.

The executable code is run on a single board computer 4.1.1 to correct the observed values to true readings, and the single board computer, an Octagon Systems 7200 and software together being an implementation 5. The neural network runtime code is then integrated 5.2 with a data acquisition program on the single board computer 5.1, to read the transducer values 5.1.1, and apply scaling factors 5.1.2 to the raw data. The implementation 5 also includes an output system 5.3, which outputs the corrected value and displays the corrected value 5.4.

The system hardware 6 includes the single board computer 6.1, an Octagon Systems Corporation Model 7200 6.1.1, a power supply 6.2, and various hardware 6.3, including an enclosure. The system hardware 6 is interfaced to the sensors and other control systems through input/output wiring 6.4. The hardware and the software together form the entire system 7.

SYSTEM ARCHITECTURE

FIG. 1 diagrammatically shows a neural network according to the present invention. This network is a three layer feed-forward design, having four input neurons 10, 11, 12, 13, representing the four input sensors, a hidden layer having four neurons 14, 15, 16, 17, and a single output neuron 18 representing the compensated output.

Figure 2:
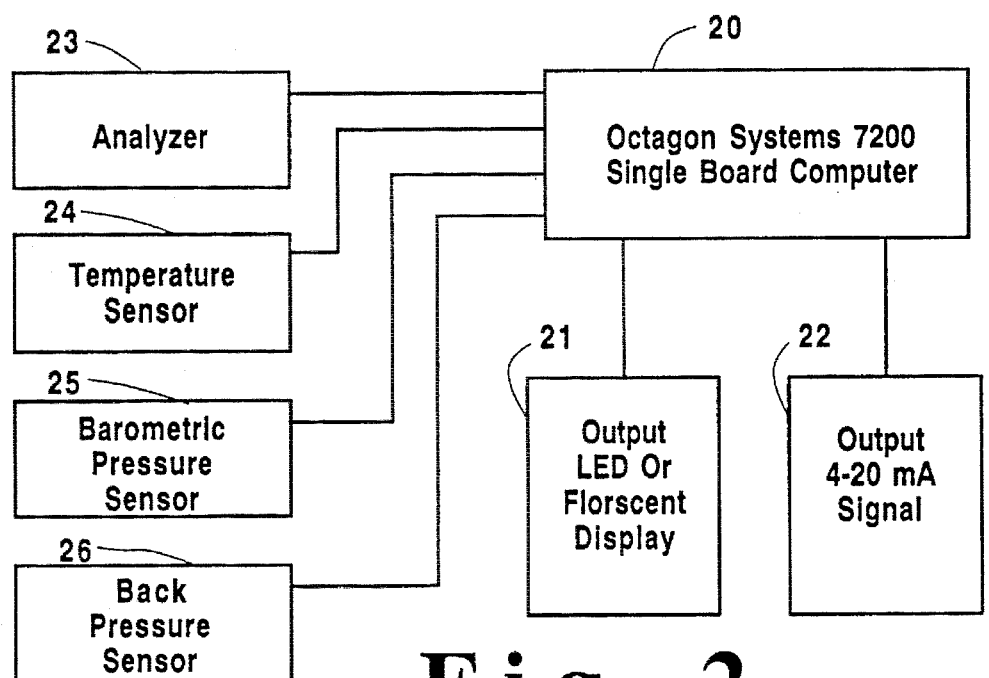
FIG. 2 shows a block diagram of a compensation network according to the present invention.

FIG. 2 shows a block diagram of a compensation network according to the present invention. The system includes a single board computer 20, an Octagon Systems 7200, which outputs to a visual display 21 and to a 4–20 mA current loop output 22. The system receives inputs from the oxygen analyzer 23, a Teledyne 3060, the temperature sensor 24, a copper constantan thermocouple, a barometric pressure sensor 25 and a back pressure sensor, a Rosemount model 1151GP4E2281.

Figure 3:
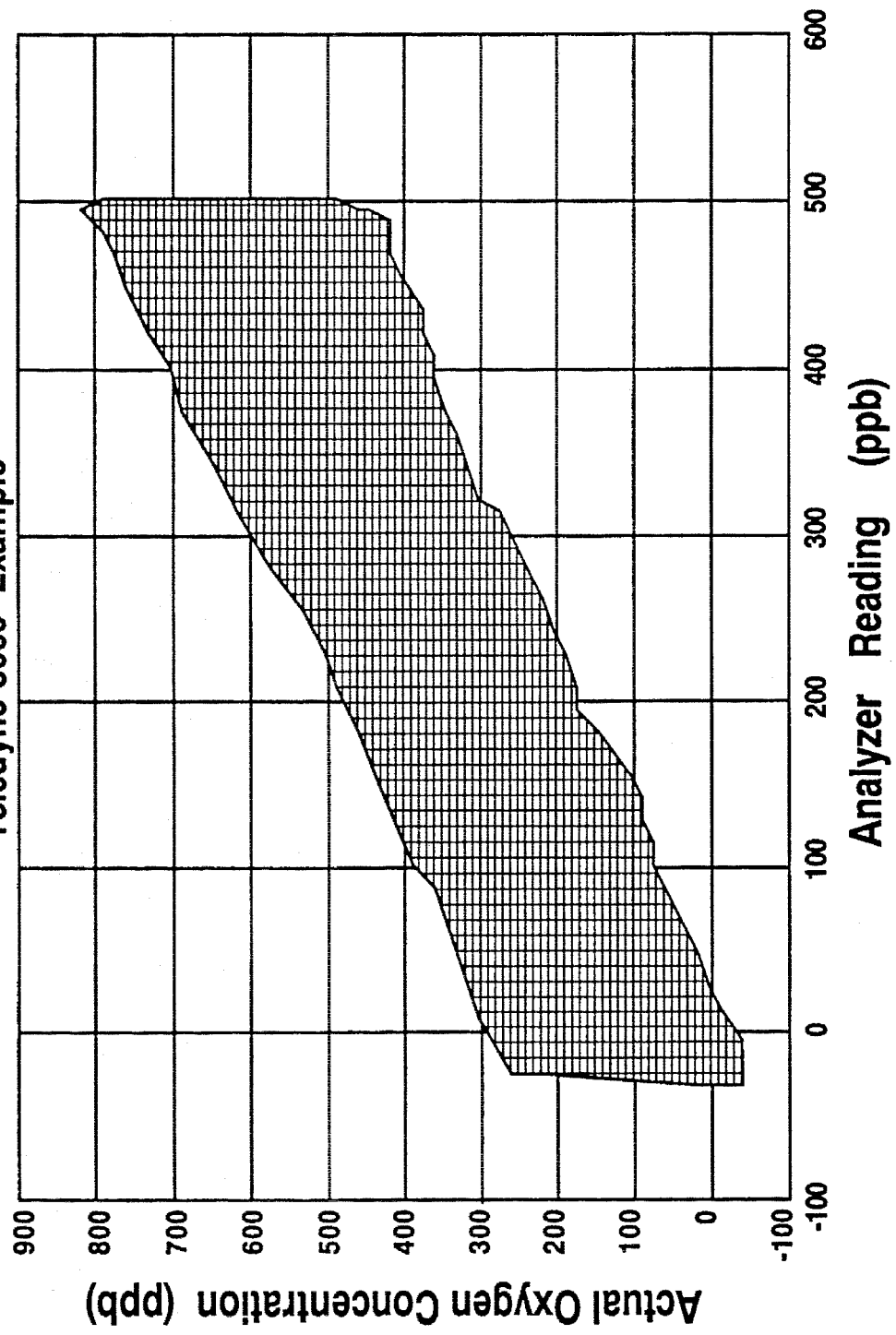
FIG. 3 is a plot of readings obtained from the analyzer under differing conditions of temperature, pressure and oxygen concentration, with statistical correction.

FIG. 3 is a plot of the individual readings obtained from the analyzer under differing conditions of temperature, pressure and oxygen concentration with statistical correction. On the other hand, FIG. 4 shows the same readings as those of FIG. 3, compensated by the neural network according to the present invention.

Figure 4:
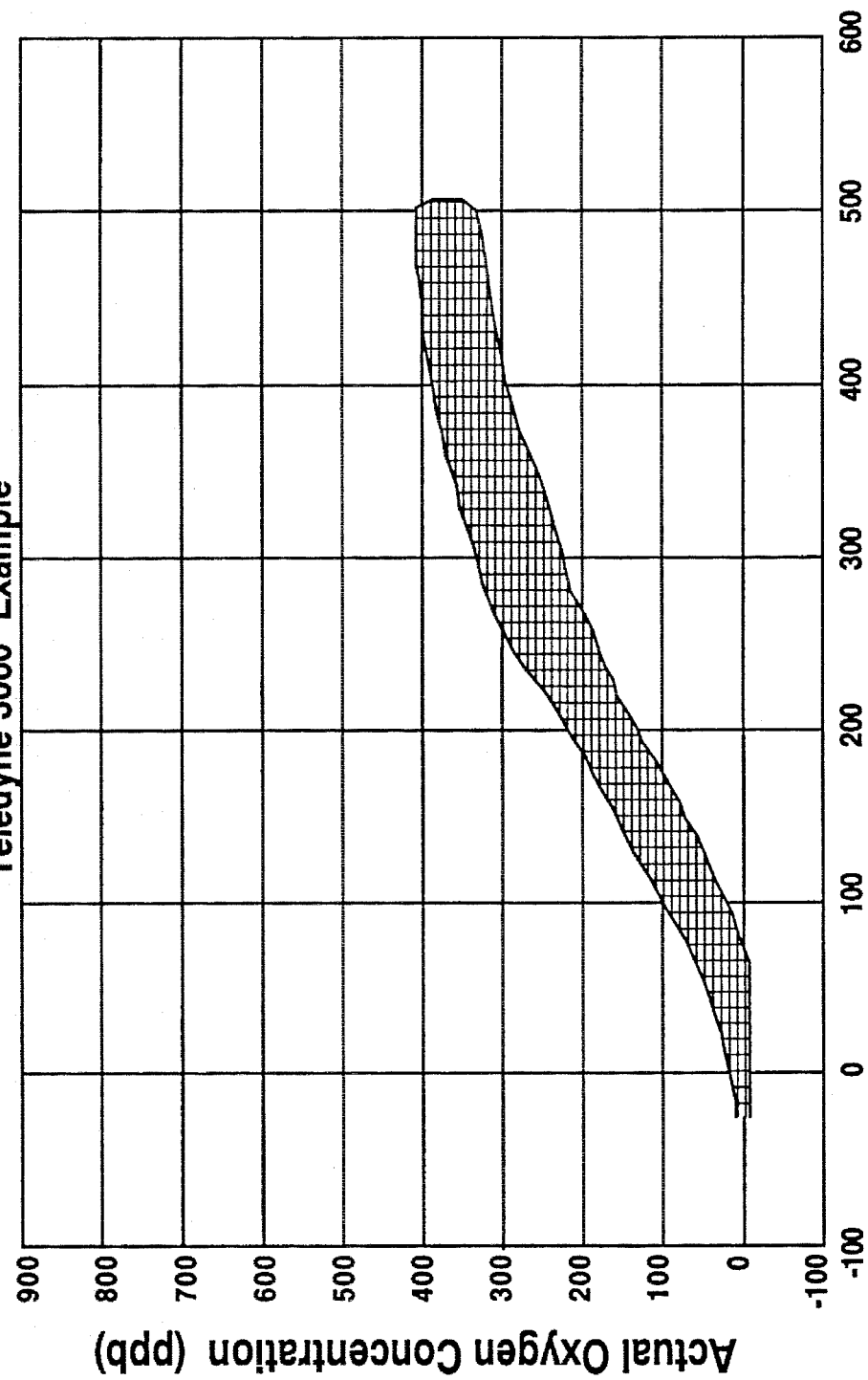
FIG. 4 is a plot of readings obtained from the analyzer under differing conditions of temperature, pressure and oxygen concentration, with neural network compensation according to the present invention.

Comparing the analyzer including compensation network according to the present invention, e.g., FIG. 4, to a statistical regression compensation system, e.g., FIG. 3, it can be seen that the neural network compensation network produces smaller errors, and in particular has greater accuracy around 0 ppb. It is noted that the statistical compensation scheme presented in FIG. 3 produces a best fit when the "actual" oxygen concentration is allowed to obtain a value below zero. Calibration data of the analyzer at different temperatures, pressures and known concentrations of oxygen were used in a regression to arrive at a mathematical formula which would correct this data for temperature and pressure variations.

Figure 5:
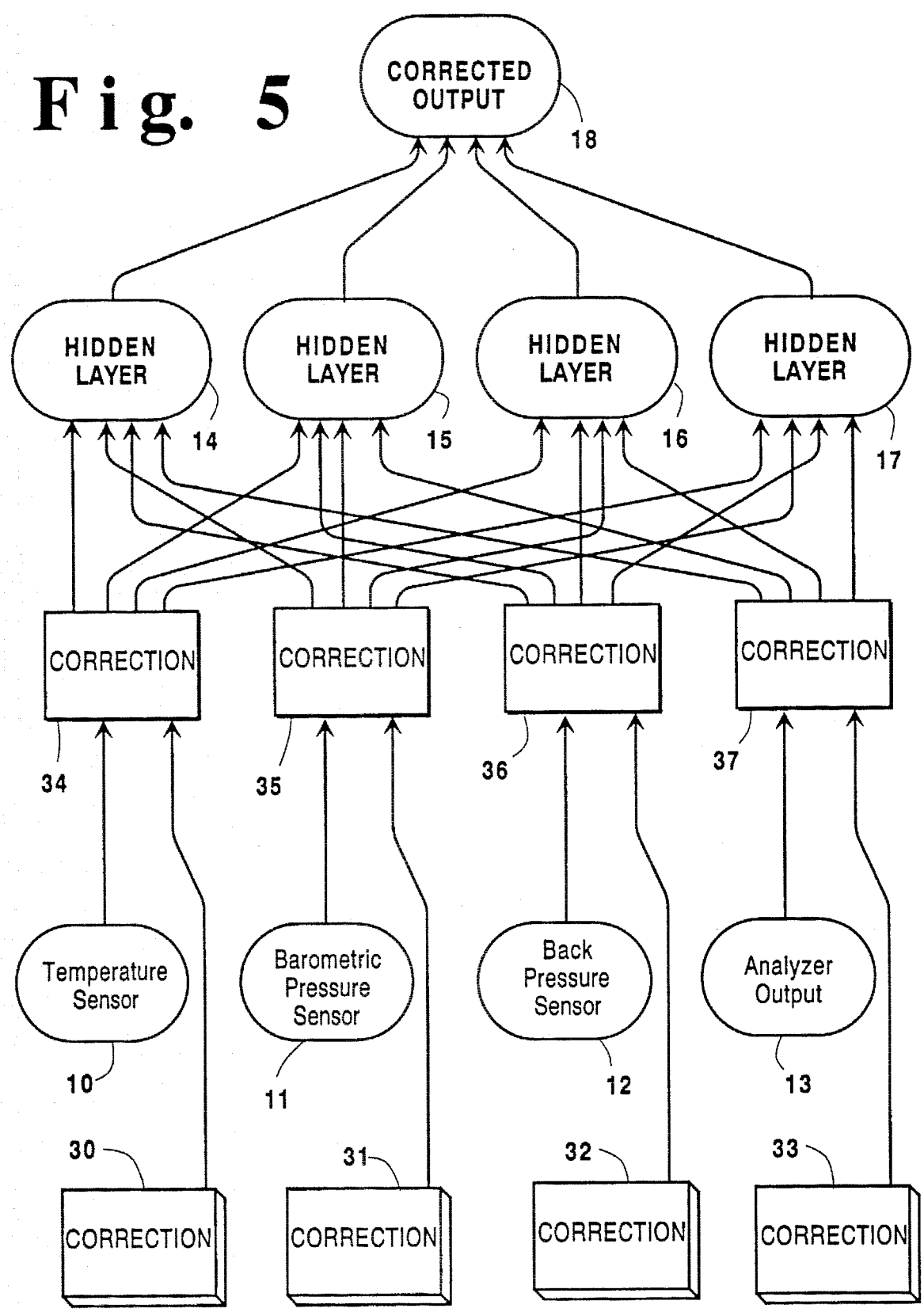
FIG. 5 is a block diagram of a neural network system having parametric-based compensation of replaceable sensors having parametric compensation data.

FIG. 5 corresponds to FIG. 1, with the addition of correction memory 30, 31, 32, 33 linked with each sensor 10, 11, 12, 13. The sensor output and the correction memory are used together in a correction 34, 35, 36, 37, to precompensate the sensor to a prototype sensor characteristic, so that the neural network remains accurate even when sensors are replaced. In practice, the correction memory 33 will be most necessary for the electrochemical cell of the analyzer 13, while it will likely be least necessary for the temperature sensor 10. The correction necessary for the pressure sensors will depend on the characteristics of the sensors employed.

EXAMPLE 2

The neural network compensation mechanism may be used to allow simplification of the gas analyzer instrument, providing accuracy, with lowered cost and improved functionality.

Figure 6:
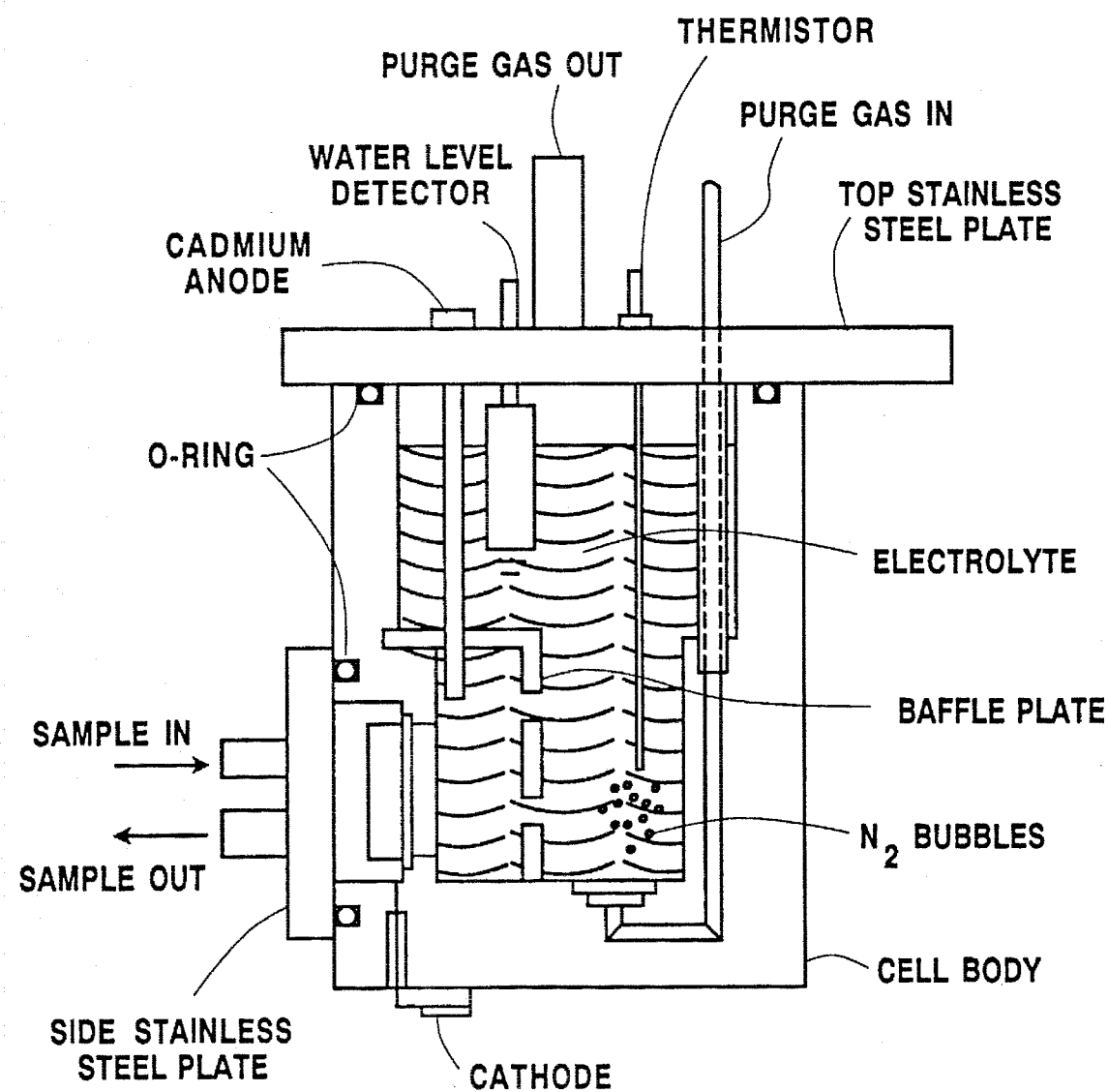
FIG. 6 is a cross section view of an electrochemical oxygen sensor employed with the present invention.

Taking, for example, the Teledyne 3060E, the sensor itself is a suitable electrochemical cell as shown in FIG. 6. This cell might be altered, however, to eliminate the sparger, which bubbles an oxygen-free gas through the electrolyte to reduce residual oxygen concentration in the electrolyte. Instead, the cell may include an electrolytic scavenging or catalytic reducing system. While this type of system may produce an increased raw error, its is not susceptible to impurities or contaminants in the sparging gas, and the error may be compensated by the neural network system.

The cell electrolyte temperature may be measured by a thermistor, as used on the Teledyne 3060E, a thermocouple, e.g., a copper constantan junction, or a silicon semiconductor temperature sensor. Unlike in the Teledyne 3060E, however, the electrochemical cell is not placed in a constant temperature oven. Rather, the cell remains at ambient temperature, and is temperature compensated by the neural network compensator.

In this instance, the cell should be isothermic, or include multiple temperature sensors, so that thermal gradients to not affect performance. Most importantly, the temperature of the cathode and anode, followed by the temperature of the bulk electrolyte are measured. Likewise, the cell should not have substantial internal pressure barriers, so that the cell is isobaric. The pressure transducer may be provided as a differential pressure device to detect the pressure difference between the gas stream to be measured and the cell.

EXAMPLE 3

Figure 7:
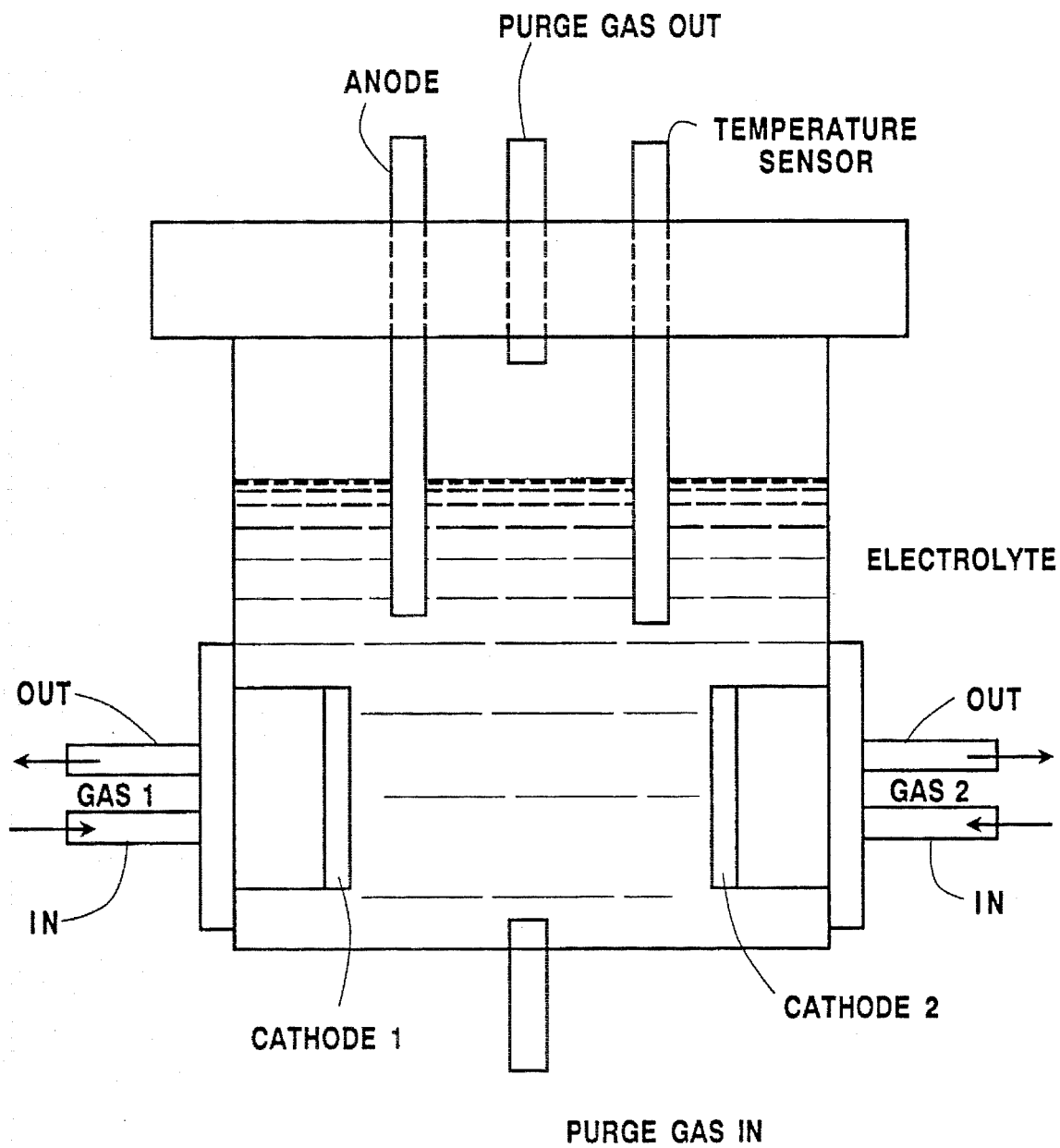
FIG. 7 is a cross section view of a dual cathode electrochemical sensor according to the present invention.

According to the present invention, an electrochemical cell may be provided with two cathodes and a common anode, as shown in FIG. 7. The cathodes may be dedicated to be process and control inputs, or may reverse periodically through valving. In this case, a measurement may be obtained in any of a number of ways. First, one cathode may be calibrated while the other obtains a measurement, periodically, these will reverse. Second, one cathode may be used to null the output of the other, allowing the oxygen concentration to be determined by the nulling concentration of oxygen. Third, a control cathode may be used to continuously characterize the cell, to provide compensation data for the active cathode.

It is noted that, where the cell is provided with an internal compensation mechanism, the neural network will perform a somewhat different function. In this case, the neural network may be used to compensate for slight differences between the two cathodes, over the range of temperatures and pressures, or to compensate for artifacts in the dual cathode compensation scheme, such as the calibration gas sources, differences in pressure between the process gas and calibration gas, characteristics of the compensating electronics, and other factors.

There has thus been shown and described a novel neural network compensation for sensors which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A method for correcting an output from an electrochemical cell sensor, having an output responsive to a concentration of sensed species in a stream, a pressure and a temperature in an interactive non-linear relationship, comprising the steps of:

(a) providing an pressure sensor for producing an output responsive to a pressure in proximity to the electrochemical sensor;

(b) providing a temperature sensor for producing an output responsive to a temperature of said electrochemical sensor; and (c) processing the outputs of the electrochemical sensor, pressure sensor and temperature sensor in a neural network having an output function which compensates said electrochemical sensor for changes in pressure and temperature to indicate a concentration of the sensed species.

2. The method according to claim 1 wherein said neural network is a three layer feedforward network trained with backpropagation of errors.

3. The method according to claim 1, further comprising the step of providing a concentration of sensed species in a stream sensed by said electrochemical sensor.

4. The method according to claim 1, further comprising the step of varying a pressure or temperature while sensing said sensed species.

5. The method according to claim 1, wherein said electrochemical sensor is responsive to an oxygen concentration in said stream.

6. The method according to claim 1, further comprising the step of providing a second pressure sensor for producing an output responsive to a barometric pressure.

7. An apparatus for compensating an electrochemical sensing apparatus, comprising:

(a) an electrochemical sensor, being responsive to a sensed species, and an environmental variable;

(b) an environmental variable sensor, being responsive to said environmental variable; and (c) a compensation network for producing a compensated output based on an output of said electrochemical sensor and an output of said environmental variable sensor, said network comprising a neural network.

8. An apparatus according to claim 7, wherein said electrochemical sensing apparatus measures a concentration of a gas used for semiconductor fabrication.

9. The apparatus according to claim 7, wherein neural network comprises an input layer, a hidden layer and an output layer in a feedforward arrangement, having inputs to said input layer from said electrochemical sensor and said environmental variable sensor, wherein said electrochemical sensor, and said environmental sensor have a cross responsivity to a system condition, and wherein said electrochemical sensor, and said environmental variable sensor have a non-linear interactivity, weighted connections between said input layer and said hidden layer, weighted connections between said hidden layer and said output layer, and an output from said output layer.

10. The apparatus according to claim 7, further comprising a plurality of environmental variable sensors, said electrochemical sensing cell having a non-linear response to a plurality of environmental variables sensed by said plurality of environmental variable sensors, said neural network compensation network producing a compensated output based on an output of said electrochemical sensor and outputs of said plurality of environmental variable sensors.

11. The apparatus according to claim 10, wherein:

said electrochemical sensing cell is responsive to the sensed component and a plurality of environmental conditions;

said plurality of environmental sensors are each responsive to at least one of said plurality of environmental conditions, said environmental conditions sensed by said environmental sensors including those environmental conditions to which said electrochemical sensing cell is responsive; and said compensation network compensates the output of said electrochemical cell for said plurality of environmental conditions and linearizes said output of said electrochemical sensing cell.

12. A neural network for temperature and pressure compensating an electrochemical cell sensor responsive to a component of a stream, comprising:

an electrochemical cell sensor input, a temperature sensor input, and a pressure sensor input; and a neural network compensation network, trained to produce a compensated output representing a stream component concentration from said electrochemical cell sensor input, temperature sensor input and pressure sensor input.

13. The system according to claim 12, wherein said pressure sensor input receives a back pressure sensor input for measuring a pressure in a gaseous medium sensed by said electrochemical cell, further comprising a barometric pressure sensor input, for measuring an environmental pressure, wherein said compensation network receives an input from said back pressure sensor, and compensates said electrochemical sensor cell for the back pressure of the gaseous medium.

14. The system according to claim 12, wherein said neural network compensation network is trained by a back propagation of error method in a training phase.

15. The system according to claim 12, wherein said neural network receives calibration data input from a replaceable electrochemical sensor.

16. The system according to claim 12, further comprising a partial response maximum likelihood predictive system for anticipating an output value after settling.

17. The system according to claim 12, further comprising a humidity sensor input, said compensation network receiving said humidity sensor input.

18. The system according to claim 12, further comprising a thermostatically controlled enclosure for an electrochemical sensor cell.

19. The system according to claim 12, further comprising a controlled pressure enclosure for an electrochemical sensor cell.

20. The system according to claim 12, further comprising a pressure regulator to regulate a back pressure of a stream sensed by an electrochemical sensor cell.

* * * * *